United States Patent
Train

(10) Patent No.: US 11,751,806 B2
(45) Date of Patent: Sep. 12, 2023

(54) BIOPHOTONIC MEDICAL IMAGING DEVICE FOR DETECTION OF ABNORMALITIES IN HUMAN TISSUE AND METHODS FOR USING SAME

(71) Applicant: Tyler Richard Train, Agoura Hills, CA (US)

(72) Inventor: Tyler Richard Train, Agoura Hills, CA (US)

( * ) Notice: Subject to any disclaimer, the term of this patent is extended or adjusted under 35 U.S.C. 154(b) by 821 days.

(21) Appl. No.: 16/785,631

(22) Filed: Feb. 9, 2020

(65) Prior Publication Data
US 2021/0045681 A1 Feb. 18, 2021

Related U.S. Application Data

(60) Provisional application No. 62/885,759, filed on Aug. 12, 2019.

(51) Int. Cl.
*A61B 5/00* (2006.01)
*A61F 2/12* (2006.01)

(52) U.S. Cl.
CPC .......... *A61B 5/4851* (2013.01); *A61B 5/0075* (2013.01); *A61B 5/0091* (2013.01); *A61B 5/6835* (2013.01); *A61F 2/12* (2013.01); *A61B 2562/0238* (2013.01)

(58) Field of Classification Search
CPC .................................................. A61B 5/4851
See application file for complete search history.

(56) References Cited

U.S. PATENT DOCUMENTS

| | | | |
|---|---|---|---|
| 4,795,463 A | 1/1989 | Gerow | |
| 5,423,334 A | 6/1995 | Jordan | |
| 6,122,042 A * | 9/2000 | Wunderman | A61B 1/0684 356/73 |
| 6,690,958 B1 | 2/2004 | Walker et al. | |
| 8,060,189 B2 | 11/2011 | Ben Dor et al. | |
| 2009/0012372 A1 | 1/2009 | Burnett et al. | |
| 2018/0042583 A1* | 2/2018 | Pringle | A61B 8/13 |

FOREIGN PATENT DOCUMENTS

| | | |
|---|---|---|
| EP | 0177288 A2 | 4/1986 |
| EP | 0928156 B1 | 8/1996 |
| RU | 2364339 C1 | 8/2009 |

OTHER PUBLICATIONS

Frank et al. Detection of Silicon in Lymph Node Biopsy Specimens by Near-Infrared Raman Spectroscopy, Applied Spectroscopy vol. 47, No. 4, 1993. (Year: 1993).*
Light scattering breast implant, Research Disclosure, published Sep. 1998. (Year: 1998).*
Wold, Jens Petter, et al. "Near-Infrared Spectroscopy Detects Woody Breast Syndrome in Chicken Fillets by the Markers Protein Content and Degree of Water Binding." Poultry Science, vol. 98, No. 1,2018, pp. 480-490., doi:10.3382/ps/pey351.
(Continued)

*Primary Examiner* — Joseph M Santos Rodriguez

(57) ABSTRACT

A biophotonic medical device for detection of abnormalities in human tissue. A method for noninvasive detection of a failed breast implant. A method for medical diagnosis of abnormalities in human tissue by adjusting the positioning of a light source and an adjacent light detector on a single surface of a target region.

20 Claims, 6 Drawing Sheets

(56) References Cited

OTHER PUBLICATIONS

Brown, SL, et al. "Prevalence of rupture of silicone gel breast implants revealed on MR imaging in a population of women in Birmingham, Alabama." Am J Roentgenol, 2000.
Van Diest, Paul, et al. "Pathology of silicone leakage from breast implants." J Clin Pathol, Mar. 1998.
Juanpere, Sergi, et al. "Imaging of Breast Implants—a Pictorial Review." Insights into Imaging, vol. 2, No. 6, Jul. 2011, pp. 653-670.
Srinivasan, Subhadra, et al. "Image guided near-infrared spectroscopy of breast tissue in vivo using boundary element method." J Biomed Opt, vol. 15, No. 6, Nov. 2010.
Kidder, Linda, et al. "Visualization of silicone gel in human breast tissue using new infrared imaging spectroscopy." Nature Medicine, vol. 3, No. 2, Feb. 1997.
Strangman, Gary, et al. "Depth Sensitivity and Source-Detector Separations for Near Infrared Spectroscopy Based on the Colin27 Brain Template." PLoS ONE, 2013.
Henderson, Theodore, and Larry Morries. "Near-infrared photonic energy penetration: can infrared phototherapy effectively reach the human brain?" Neuropsychiatric Disease and Treatment, 2015, pp. 2191-2208.
Leon-Carrion, Jose, et al. "The Infrascanner, a handheld device for screening in situ for the presence of brain haematomas." Brain Injury, Sep. 2010, pp. 1193-1201.
Lanzarotta, Adam, and Caroline M. Kelley. "Forensic Analysis of Human Autopsy Tissue for the Presence of Polydimethylsiloxane (Silicone) and Volatile Cyclic Siloxanes using Macro FT-IR, FT-IR Spectroscopic Imaging and Headspace GC-MS." J Forensic Sci, 2016.
Delpy, D.T., and M. Cope. "Quantification in Tissue near-Infrared Spectroscopy." Phil. Trans. R. Soc. Long., 1997.

\* cited by examiner

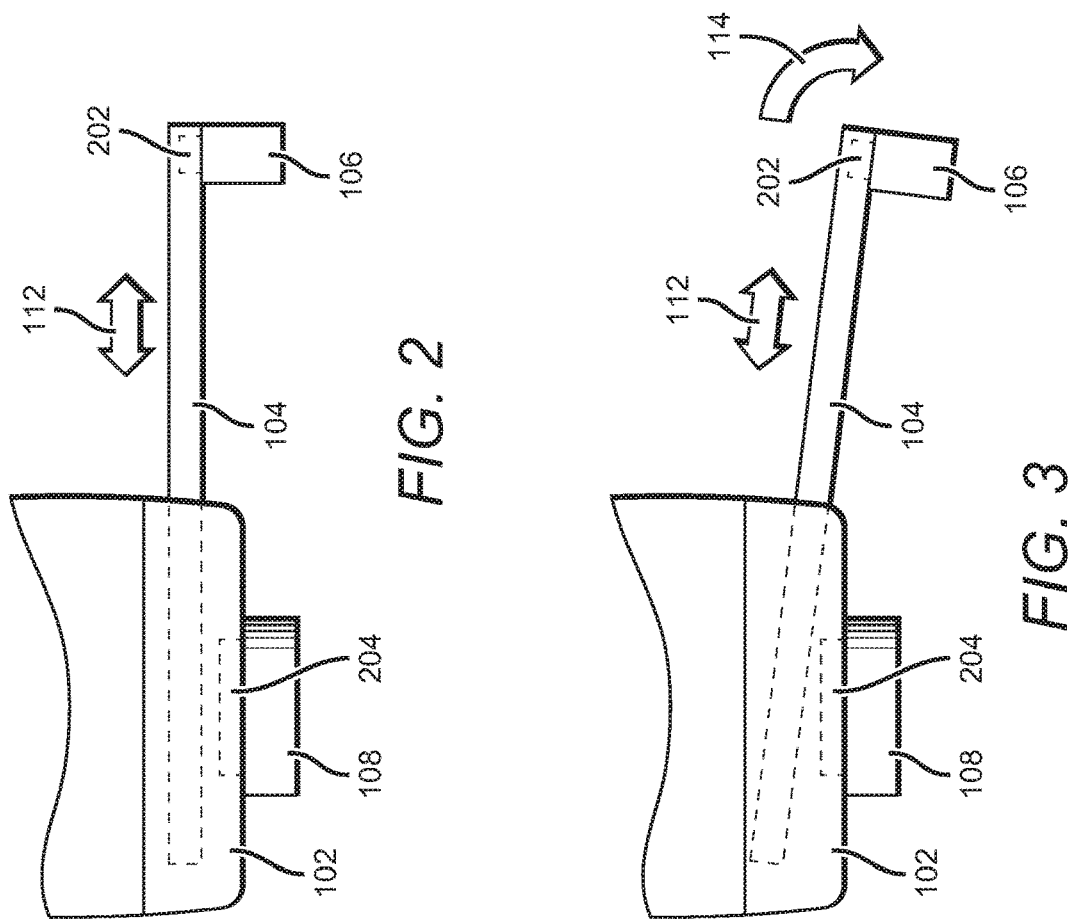
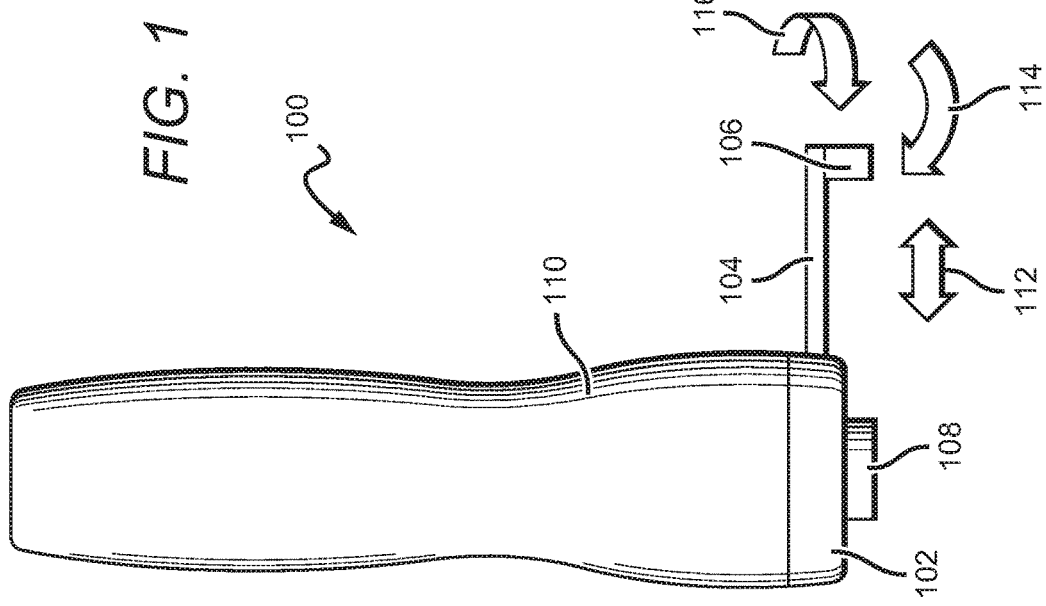

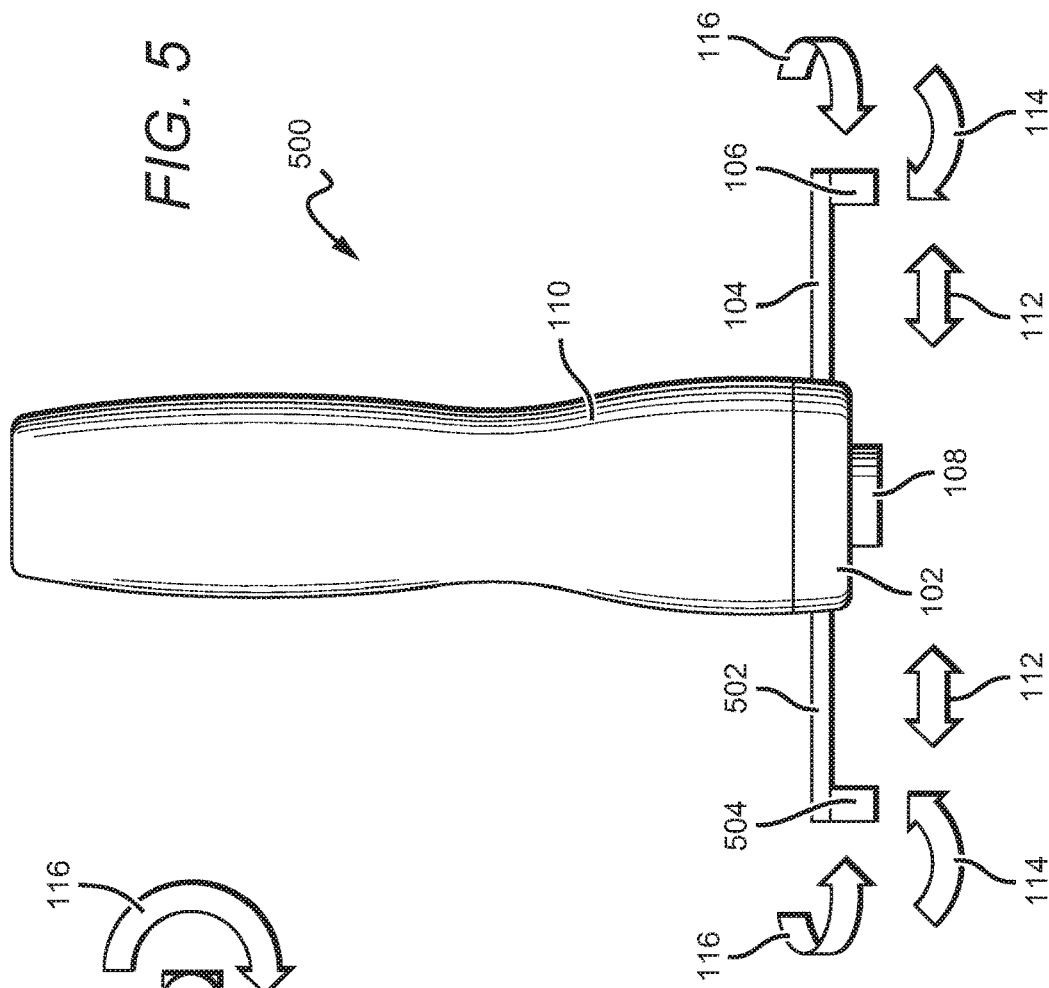
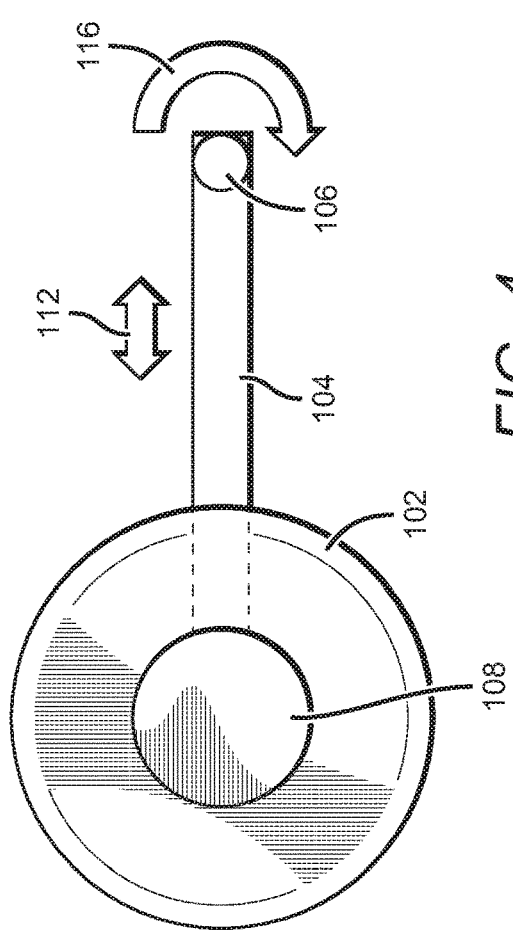

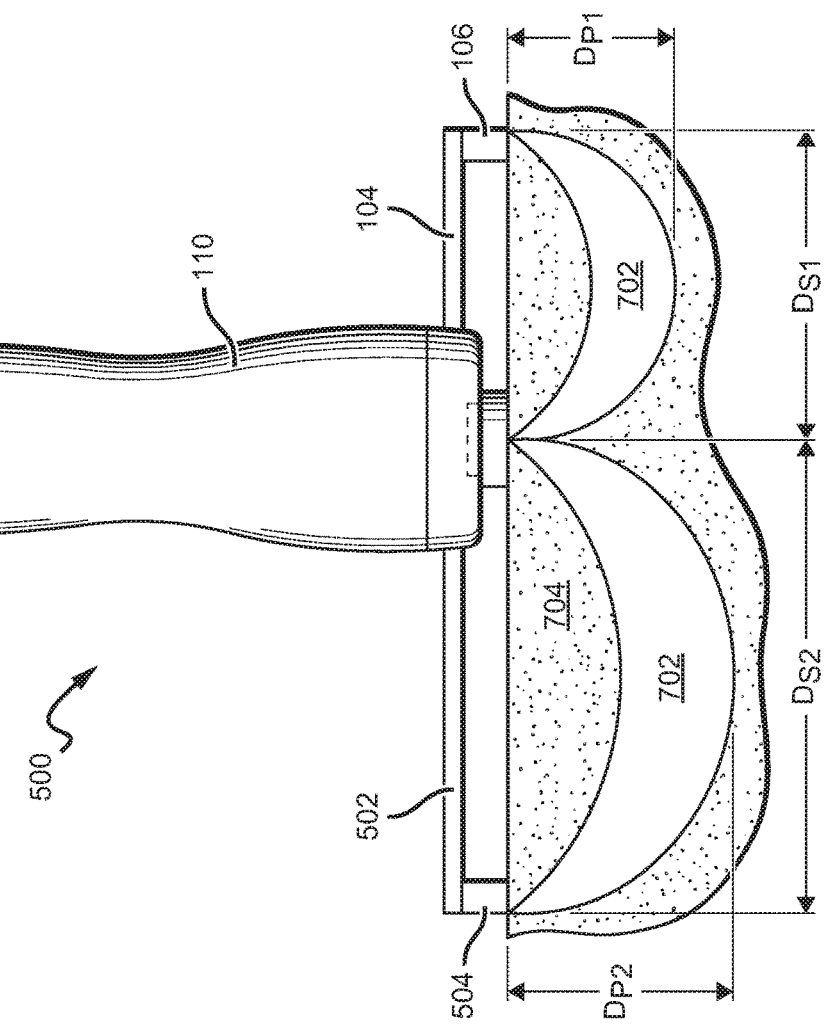
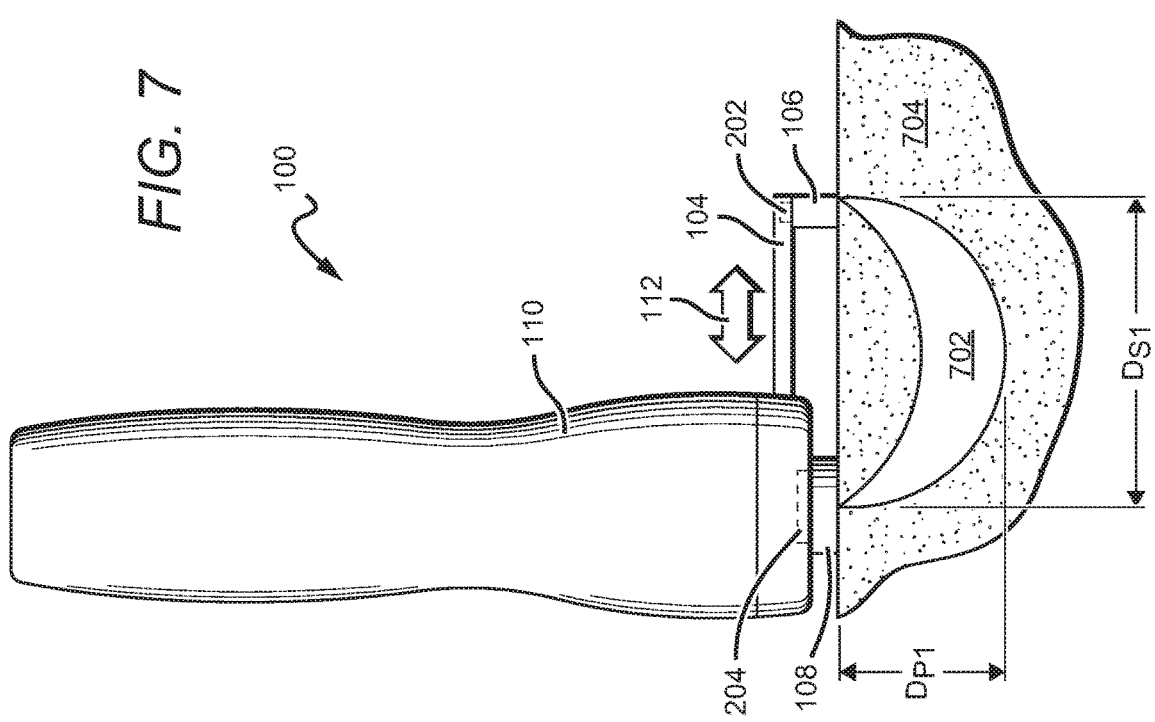

BIOPHOTONIC MEDICAL IMAGING DEVICE FOR DETECTION OF ABNORMALITIES IN HUMAN TISSUE AND METHODS FOR USING SAME

RELATED APPLICATION

This application claims the benefit of priority of U.S. Provisional Application No. 62/885,759 entitled BIOPHOTONIC MEDICAL IMAGING DEVICE FOR NONINVASIVE IN VIVO DETECTION OF ABNORMALITIES IN HUMAN TISSUE AND METHODS FOR USING SAME, filed Aug. 12, 2019. The contents of this application are hereby incorporated by reference herein in their entirety.

FIELD OF THE INVENTION

The present disclosure relates to the field of medical devices. More specifically, embodiments of the present disclosure relate to a device that transmits light in the red or near infrared (NIR) region of the electromagnetic spectrum for noninvasive sensing of abnormalities in human tissue and methods for using the same. In some embodiments, the device can be used to detect failed breast implants in human breast tissue.

BACKGROUND OF THE INVENTION

An implant is a man-made medical device that is placed inside or on the surface of the body of a patient, usually through a surgical procedure. Implants have been manufactured and used for purposes such as supporting a damaged biological structure, replacing a missing biological structure, or enhancing an existing biological structure.

A breast augmentation, also known as augmentation mammoplasty, is a surgical procedure to enhance the size and/or shape of a patient's breast. Similarly, a breast reconstruction is a surgical procedure that restores the shape of the breast of a patient who is having or has recently undergone a breast mastectomy (a surgical procedure that removes the patient's breast tissue to treat or prevent breast cancer). During breast augmentations and breast reconstructions, plastic surgeons may use breast implants filled with a saline solution, silicone gel, a combination of both, or even other filler material. During a breast augmentation surgery, a plastic surgeon places a breast implant under the patient's breast tissue or chest muscle. For an immediate breast reconstruction surgery (i.e., a breast reconstruction performed at the same time as a mastectomy), the implant is generally placed under the chest muscle due to the lack of remaining breast tissue. A delayed breast reconstruction surgery (i.e., a breast reconstruction performed in a subsequent procedure from a mastectomy) usually involves placing a short-term tissue expander in the breast and later introducing a breast implant.

Breast implants typically consist of a shell (also known as the envelope), filler (e.g., silicone and/or saline), and a patch (to cover a manufacturing hole). One inherent risk associated specifically with placing a silicone breast implant into a patient's body is the potential that the implant shell may fail, resulting in possible leakage, breakage, or rupture (hereinafter collectively, "failure" or "rupture") and leak the filler silicone into the surrounding areas of the breast and possibly other areas of the patient's body. As used herein, "rupture" is not intended to limit the present disclosure to exclude other types of breast implant failures such as leakage. There are many reasons why a failure may occur such as damage to the implant during implantation or other surgical procedures, folding or wrinkling the implant shell, traumatic force to the breast and chest area, or required compression during mammography. Additionally, the shell may be smooth or textured, which could further affect whether an implant fails. One study on silicone breast implant rupture revealed that 77% of women with silicone breast implants in the study had at least one breast implant that was ruptured or suspicious for rupture. That study explained that eventually all silicone implants will fail, with the average lifespan of an implant being 10.8 years.

Leaked silicone from failed breast implants has been associated with a number of various pathologies such as lymphoma, metaplasia, and carcinoma. Failure to detect failures early can lead to spreading of leaked silicone that can present other health issues. For instance, if silicone reaches the lymph nodes, the lymph nodes can be phagocytized by multi-nucleated giant cells. In 1992, the Food and Drug Administration (FDA) placed a ban on silicone breast implants due to concerns associated with leaked silicone, only allowing certain silicone breast implants back on the market under strict conditions in 2006. Due to the risks associated with failed breast implants, it is important for patients with silicone breast implants to schedule regular implant failure tests. It is recommended that patients are tested three years after the initial implantation and every two years thereafter.

Currently, the most common test to detect a failed silicone breast implant is through magnetic resonance imaging (MRI). However, there are limitations to MRIs that can prevent patients from obtaining frequent testing. For example, patients with metal in their body or claustrophobia generally cannot undergo an MRI. Additionally, an MRI is a time-consuming procedure, and the high costs associated with MRI testing generally discourage patients from obtaining frequent MRI tests, especially when their health insurance will not cover the procedure. Computed tomography (CT) and ultrasonography (US) have also been implemented for implant failure, but these also involve complex and costly methods that can serve as a deterrent to patients. MRIs are also generally large devices and size/cost limitations of MRIs can prevent certain hospitals, such as those in rural areas, from housing and performing MRI testing on patients. Therefore, some patients may need to travel long distances in order to obtain an MRI from a larger hospital and a need exists for a smaller, portable detection device.

Different attempts have been made in the prior art to provide alternative rupture detection systems. However, many of these attempts require use of a specialized or altered breast implant at the time of augmentation or reconstruction surgery and are not suitable for widespread detection of commonly used implants. For example, U.S. Pat. No. 4,795,463 to Gerow discloses a breast implant filled with silicone, saline, or a combination contained inside a silicone elastomer envelope that is labeled with radioopaque markers. The markers are configured to absorb electromagnetic energy differently from the envelope, its contents, and the surrounding human tissue such that a rupture in the envelope can be detected by roentgenographic imaging.

U.S. Pat. No. 5,423,334 to Jordan discloses a system for acquiring data from a characterization tag secured to a medical device implanted inside a patient's body. The characterization tag is powered by energy absorbed through the mutual inductive coupling of circuitry in the tag with an alternating magnetic field that is generated outside of the patient's body, which allows for the sensing of variations in the amount of energy absorbed from the magnetic field by the characterization tag.

U.S. Patent Publication No. 2009/0012372 to Burnett, et al. discloses a system for detecting implant rupture comprising a sensor coupled to an outer surface of a breast implant and configured to measure a property at the outer surface that is indicative of implant rupture such as electrical conduction, chemical composition, or an optical property.

One limitation of detection systems similar to those discussed above is that they require specialization or alteration of the breast implant prior to implantation so that the implant can participate in the communication of information from within the body. This creates problems for the majority of patients with common implants that are not configured to communicate such information. Accordingly, a system is needed that can detect implant failure from all types of implants, while requiring less complex, intensive, and/or costly means as compared to MRI, CT, and US.

One method for less complex and expensive imaging known generally in the art is through the use of NIR technology. NIR spectroscopy and imaging are analytical noninvasive techniques that use the NIR region of light (800-2500 nm) to determine the composition of a target sample. When NIR light is directed at a target sample, some of the light scatters and passes back to the surface of the sample through what is known as a "banana-shaped" photon path. This allows for a light detector (such as a photodiode) that is placed near a NIR light source on the same side of a thick target sample (such as a human head or breast) to analyze superficial portions of the tissue. The light that returns to the detector contains information about the vibrational absorption characteristics of the target sample that it has just interacted with, allowing for chemical composition analysis of the target sample. Studies have shown that increasing the separation distance between the source and detector increases penetration depth sensitivity. Other factors may also be involved in determining penetration depth such as wavelength and the type of tissue targeted.

Because of its interaction with human blood, NIR light has largely been used for diagnosis of blood-related medical conditions such as diabetes and hematoma and for studying cerebral blood flow through a process known as function near infrared spectroscopy (fNIRS). For example, U.S. Pat. No. 8,060,189 discloses a system for determining brain hematoma with a NIRS device. The devices uses near infrared light to determine the optical density of various regions of the brain. However, the present disclosure explains that NIR light can also be used to detect the presence of leaked filler from a breast implant, which generally appear as small round or irregular translucent droplets of amorphous retractile material.

At least two studies have used NIR light to detect the presence of silicone gel in human breast tissue. These studies identified certain vibrational absorption bands for detection of silicone, such as a peak in the vibrational absorption band at 2850-3000 $cm^{-1}$, which is characteristic of the $CH_3$ bonds in silicone. In contrast to the present disclosure, these studies were performed in vitro with prepared biopsy samples. Requiring a patient to take a biopsy for regular testing every two years is undesirable and unlikely to provide a practical clinical alternative to MRI testing.

It is an object of certain embodiments of the present disclosure to provide a device that is capable of performing in vivo detection of leaked filler material and/or ruptured breast implant in human breast tissue using red or NIR light.

It is another object of certain embodiments of the present disclosure to provide methods for medical diagnostic procedures using photonics to detect abnormalities in human tissue.

SUMMARY OF THE INVENTION

Certain embodiments of the present disclosure relate to a biophotonic medical device for noninvasive in vivo detection of abnormalities in human tissue. In some embodiments, the device comprises at least one adjustable arm that can adjust in at least one direction to control effective positioning of a source and a detector across a planar or nonplanar surface of a target region. In other embodiments, the device comprises a plurality of adjustable arms that are adjustable in a plurality of directions. In still other embodiments, a single arm may comprise a plurality of sources and/or a plurality of detectors and may further comprise one or more joints to provide the device with even more degrees of freedom. Increasing the number of arms, sources, detectors, and/or degrees of freedom for directional adjustment can provide greater control, variability, and customization for a medical testing apparatus.

Some embodiments of the present disclosure are directed to a method for medical diagnosis. In certain of these embodiments, the method is for in vivo detection of a failed breast implant. In other embodiments, the method comprises making adjustments to a sensor device to correspond to a desired setting, for example, a desired penetration depth and/or for proper application to a particular surface area.

These and other further features and advantages provided in this disclosure would be apparent to those skilled in the art from the following detailed description, taken together with the accompanying drawings.

BRIEF DESCRIPTION OF THE DRAWINGS

FIG. 1 shows a biophotonic device according to certain embodiments of the present disclosure.

FIG. 2. illustrates a first direction of adjustability for the device according to certain embodiments of the present disclosure.

FIG. 3. illustrates a second direction of adjustability for the device according to certain embodiments of the present disclosure.

FIG. 4. illustrates a third direction of adjustability for the device according to certain embodiments of the present disclosure.

FIG. 5 shows another embodiment of a biophotonic device according to the present disclosure comprising two adjustable arms.

FIG. 7 illustrates the photon path of light transmitted from a source to an adjacent detector on the same surface of a target region.

FIG. 8 shows one embodiment of a biophotonic device according to the present disclosure wherein two sources adjusted to different separation widths are transmitting light to one detector from a single surface of a target region.

DETAILED DESCRIPTION OF THE INVENTION

Figure 6:
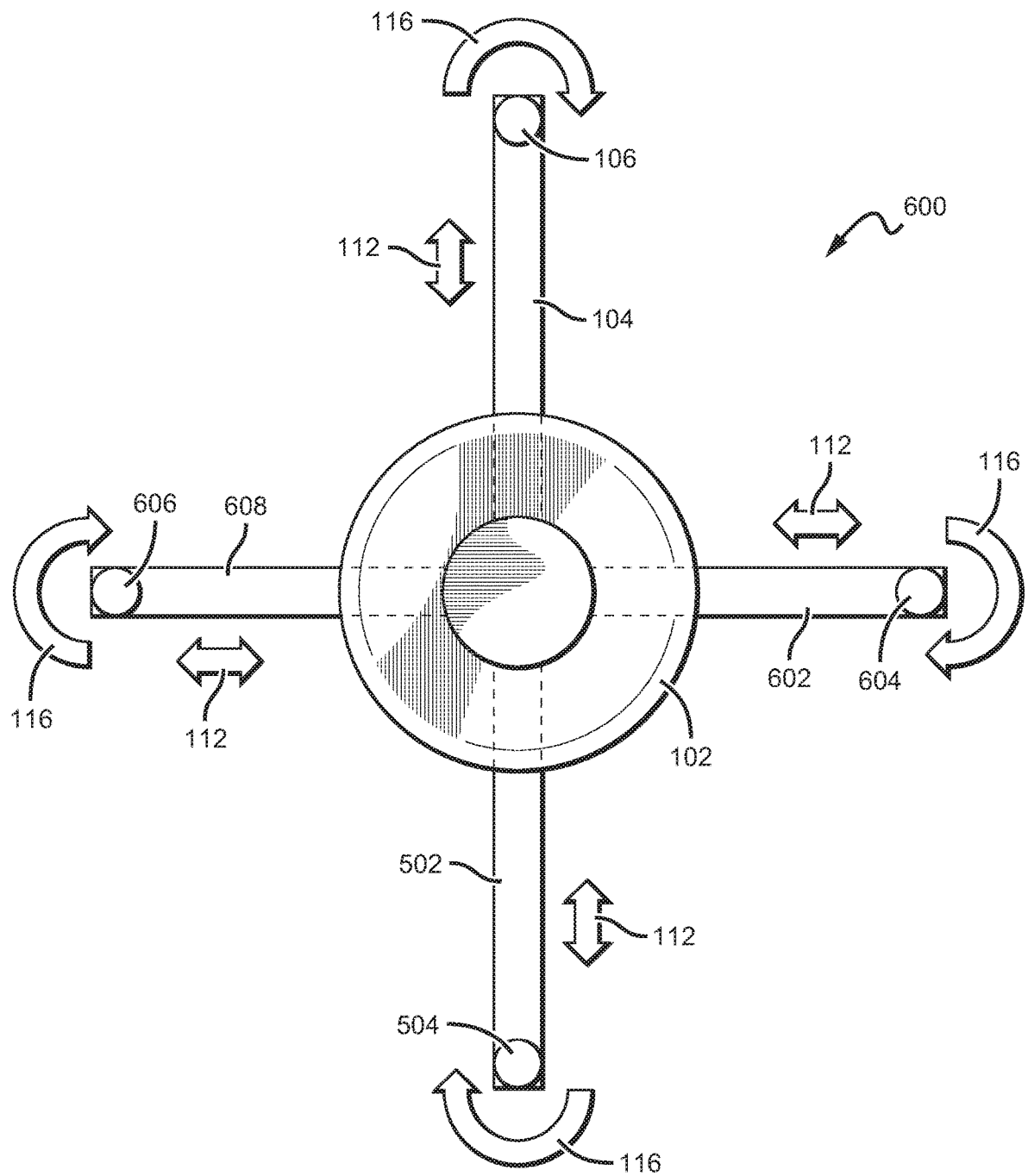
FIG. 6 shows yet another embodiment of a biophotonic device comprising four adjustable arms.

Throughout this disclosure, the embodiments illustrated should be considered as exemplars, rather than as limitations on the present disclosure. As used herein, the term "invention," "device," "apparatus," "method," "disclosure," "present invention," "present device," "present apparatus," "present method," or "present disclosure" refers to any one of the embodiments of the disclosure described herein, and any equivalents. Furthermore, reference to various features of the "invention," "device," "apparatus," "method," "disclosure," "present invention," "present device," "present apparatus," "present method," or "present disclosure" throughout this document does not mean that all claimed embodiments or methods must include the reference features.

It is also understood that when an element or feature is referred to as being "on" or "adjacent" to another element or feature, it can be directly on or adjacent the other element or feature or intervening elements or features may also be present. In contrast, when an element is referred to as being "directly on" or extending "directly onto" another element, there are no intervening elements present. Additionally, it is understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

Furthermore, relative terms such as "inner," "outer," "upper," "top," "above," "lower," "bottom," "beneath," "below," and similar terms, may be used herein to describe a relationship of one element to another. Terms such as "higher," "lower," "wider," "narrower," and similar terms, may be used herein to describe angular relationships. It is understood that these terms are intended to encompass different orientations of the elements or system in addition to the orientation depicted in the figures.

Although the terms first, second, third, etc., may be used herein to describe various elements, components, regions, and/or sections, these elements, components, regions, and/or sections should not be limited by these terms. These terms are only used to distinguish one element, component, region, or section from another. Thus, unless expressly stated otherwise, a first element, component, region, or section discussed below could be termed a second element, component, region, or section without departing from the teachings of the present disclosure. As used herein, the term "and/or" includes any and all combinations of one or more of the associated list items.

The terminology used herein is for the purpose of describing particular embodiments only and is not intended to be limiting of the disclosure. As used herein, the singular forms "a," "an," and "the" are intended to include the plural forms as well, unless the context clearly indicates otherwise. For example, when the present specification refers to "an" assembly, it is understood that this language encompasses a single assembly or a plurality or array of assemblies. It is further understood that the terms "comprises," "comprising," "includes," and/or "including" when used herein, specify the presence of stated features, integers, steps, operations, elements, and/or components, but do not preclude the presence or addition of one or more other features, integers, steps, operations, elements, components, and/or groups thereof.

Embodiments as described in the present disclosure can be described herein with reference to view illustrations, some of which are schematic in nature. As such, the actual thickness of elements can be different, and variations from the shapes of the some of the illustrations as a result, for example, of manufacturing techniques and/or tolerances are expected. Thus, the elements illustrated in some of the figures are schematic in nature and their shapes are not intended to illustrate the precise shape of a region and are not intended to limit the scope of the disclosure.

FIGS. 1-2 show one embodiment of a biophotonic device 100 according to the present disclosure. Device 100 may comprise a base 102, which may further comprise an arm 104, a source 202 internal to arm 104, a source guide 106 external to arm 104, a detector 204 internal to base 102, and a detector guide 108 external to base 102. In some embodiments, arm 104 is fixed in place. In other embodiments, arm 104 is adjustable in at least one direction 112. In still other embodiments, arm 104 is adjustable in at least two or three directions 114, 116. In some embodiments, this adjustability is controlled automatically with a motor and operating controls, while in other embodiments, the adjustability is controlled manually. In certain embodiments, source 202 is configured to emit light with a wavelength in either the red or near infrared region of the electromagnetic spectrum and detector 108 is configured to receive some of said light from source 202. As used herein, the red region of the electromagnetic spectrum is associated with wavelengths around the range of 400-700 nm and the near infrared region of the electromagnetic spectrum is associated with wavelengths around the range of 700-2500 nm. In some embodiments, source 202 is a light emitting diode (LED) or a laser diode and detector 204 is a photodiode. Device 100 may further comprise a housing element 110, which may serve as a handle for operating device 100 and/or for housing electronic components. In some embodiments, device 100 is a portable and/or handheld device. In other embodiments, device 100 is a larger apparatus not capable of being handheld.

Figure 9:
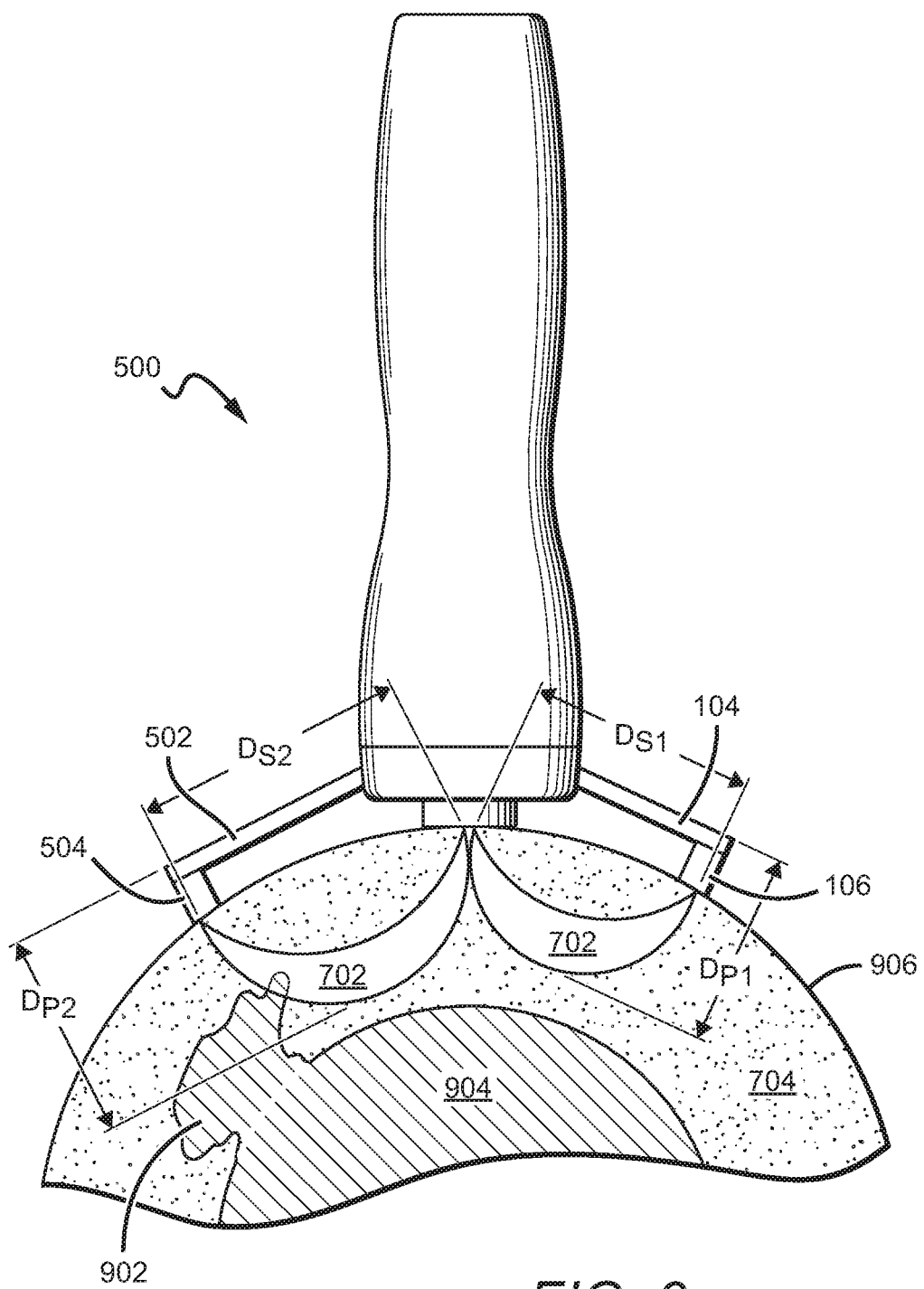
FIG. 9 shows one embodiment of a biophotonic device according to the present disclosure wherein two sources adjusted to different separation widths and different angular rotations are transmitting light to one detector from a single surface of a target region in order to detect an abnormality in the target region.

As shown in FIGS. 2-4, arm 104 may be adjustable in a plurality of directions to allow for a customizable medical testing apparatus. For example as shown in FIG. 2, arm 104 may adjust in a first direction 112, which would allow for an operator of device 100 to vary the separation width between source 202 and detector 204. Varying the separation width between source 202 and detector 204 will affect the penetration depth of the light received by detector 204 as shown in FIGS. 7-9 and discussed further below. Additionally, as source 202 is moved closer to detector 204, the signal strength received by detector 204 will increase.

FIG. 3 shows one embodiment according to the present disclosure where arm 104 is adjustable in a first and second direction 112, 114. In addition to varying the source-detector separation width by adjusting arm 104 in first direction 112, arm 104 may also be angularly rotated in second direction 114. Adjusting arm 104 in second direction 114 could allow an operator to conform device 100 to the surface of a target region 704. This could be especially useful for situations where target region 704 is not planar, such as with a human breast or human head. Because one patient's physical anatomy may differ significantly from another patient's physical anatomy, adjusting arm 104 in direction 114 could provide a highly customizable testing apparatus for a wide range of patients. This variability could be particularly useful, for example, in testing for a failed breast implant because a single device could be used across all areas of a patient's breast and across a wide variety of breast sizes and shapes.

As shown in FIG. 4, arm 104 may also be adjustable in a third direction 116. Adjustability in direction 116 allows an operator to radially vary arm 104 to a desired position. This variability could be useful for a number of reasons. For example, radially adjusting arm 104 could allow an operator to leave detector 204 in one place while taking measurements from source 202 at different positions of up to 360 degrees around detector 204. Additionally, if controls or displays are present on the body of housing 110, an operator could keep the control or display facing side of housing 110 toward himself while taking up to 360 degree measurements from source 202.

FIG. 5 shows another embodiment according to the present disclosure where biophotonic device 500 comprises two arms 104, 502, each further comprising a source and a source guide 106, 504. FIG. 5 shows detector guide 108 positioned between arms 104 and 502 so that it may receive light from sources within both arms. In some embodiments, arms 104 and 502 may be fixed or adjustable in one or more directions. Incorporating a second arm 502 into base 102 allows for more control over the medical testing apparatus. The addition of second arm 502 also may provide for a more efficient testing procedure because multiple measurements can be taken from sources within each arm at a single placement location of device 500 on target region 704.

FIG. 6 shows still another embodiment according to the present disclosure. As shown, biophotonic device 600 comprises four arms 104, 502, 602, 608. As discussed above, incorporating more arms into base 102 provides further control and customizability over the medical testing apparatus and a more efficient testing procedure. Again, detector guide 102 is shown positioned in between arms 104, 502, 602, and 608. However, it is contemplated that detector guide 102 and detector 204 may be positioned in other locations relative to the one or more arms. It is further contemplated that the features and positioning shown in FIGS. 1-6 may be switched such that there is one source and source guide on base 102 with one or more detectors and detector guides positioned on the one or more arms outside of base 102. In yet other embodiments, there may be a plurality of both sources and detectors.

FIG. 7 shows device 100 transmitting light 702 from source 202 ultimately to detector 204. Source 202 emits light 702 in a particular range of wavelengths (preferably in the red or infrared region) and source guide 106 transmits light 702 to target region 704. Detector guide 108, which is positioned adjacent to source guide 106, then receives at least some of light 702 from the same surface of target region 704 as source guide 106. Detector guide 108 then transmits at least some of light 702 to detector 204. It is understood that source guide 106 and detector guide 108 may not be present in all embodiments wherein source 202 and detector 204 could be in direct contact with target region 704. In order to reduce ambient light, especially where source guide 106 and detector guide 108 are not present, the device may comprise a shield (not shown) surrounding source 202 and detector 204. The illustration in FIG. 7 is made possible because photons in light 702 scatter as they travel through target region 704 and some of light 702 follows a banana shaped photon path back toward the surface of target region 704. Although the figures herein show the transmission of light 702 assisted by source guide 106 and detector guide 108, it is understood that these may not be necessary elements for certain embodiments of the invention to function properly. In some embodiments, source 202 and detector 204 may be the only elements required for the transmission of light 702 through target region 704.

A penetration depth $D_{P1}$ of the portion of light 702 that is received by detector 204 can be determined based on a separation width $D_{S1}$ between source 202 and detector 204. Penetration depth $D_{P1}$ may be calculated as half of separation width $D_{S1}$. Therefore, adjusting arm 104 in at least direction 112 allows an operator to control the penetration depth $D_{P1}$ of light 702.

FIG. 8 shows device 500 comprising arms 502 and 104 each with a source emitting light 702. The emitted light 702 from both sources is transmitted through target region 702 and received by detector 204. FIG. 8 shows arm 502 adjusted along direction 112 to a greater separation width $D_{S2}$ from detector 204 than separation width $D_{S1}$ of arm 104. Accordingly, the penetration depth $D_{P2}$ will be greater than penetration depth $D_{P1}$. This illustrates the heighted level of control and variability offered by providing device 500 with additional arms and adjustment capabilities.

FIG. 9 shows device 500 detecting an abnormality 902 in target region 704. In FIG. 9, arms 502 and 104 have been adjusted in direction 112 and 114 in order to control the penetration depths $D_{P1}$ and $D_{P2}$ and to align device 500 with the nonplanar surface of target region 704. In some embodiments, these and other possible arm adjustments are determined by computer modeling technology taking into consideration factors such as the size, shape, contour, and contents of target region 704. In other embodiments, the arm adjustments are determined and performed manually by the operator. FIG. 9 shows target region 704 as a breast 906 with a breast implant 904 that has failed and is leaking misplaced filler 902 into undesired areas of the breast. It is understood that other abnormalities may be tested for as well, including without limitation, cancerous cells, hematomas, blood glucose levels, and blood oxygen saturation levels. In some embodiments, the device can also monitor heart rate throughout a testing procedure. As shown, abnormality 902 runs into the path of light 702 from source guide 504. When this portion of light 702 completes its transmission to detector 204, it will contain an indicator that abnormality 902 is present in target region 704. This indicator may include a vibrational absorption band between 2800-3400 cm$^{-1}$. As shown in FIG. 9, one of the benefits of certain embodiments is that detection of abnormalities (e.g., leaked silicone) can be performed in vivo (in living tissue), which obviates the need, for example, to extract biopsy samples from the body and have them tested in a laboratory setting.

Figure 10:
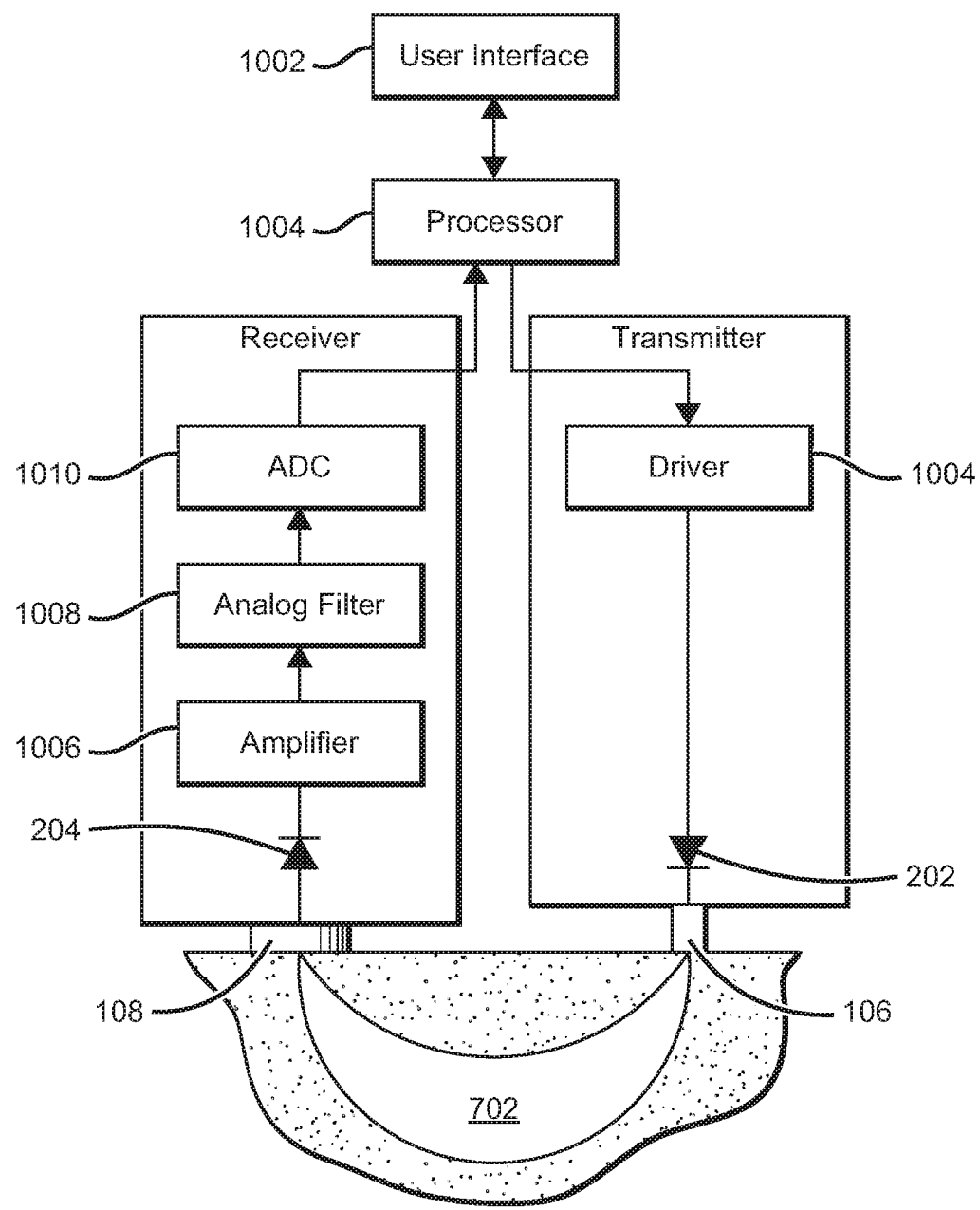
FIG. 10 shows electronic components used in generating, acquiring, and processing a signal from a biophotonic device according to certain embodiments of the present disclosure.

FIG. 10 shows a block diagram of the possible electronic components housed within housing 110 according to one embodiment of the invention. In some embodiments, a user interface 1002 communicates with a processor 1004 to send instructions and receive information from a biophotonic device. Processor 1004 may send instructions to a driver 1004, which controls the voltage output of source 202, in this case, a light emitting diode. After light 702 has been transmitted from source 202 through target region 704 to detector 204 (in this case, a photodiode), detector 204 can generate an analog signal, which can then be amplified by an amplifier 1006, filtered by an analog filter 1008 (e.g., low-pass, high-pass, or band-pass filter), and converted to a digital signal by an analog to digital converter (ADC) 1010. This digital signal can then be transmitted to processor 1004, which can process the signal (for example, through digital filtering, feature extraction, classification, etc.) and send information from the signal to user interface 1002 in an easily digestible format.

In some embodiments, user interface 1002 displays an image generated from the signal by highlighting and contrasting certain information contained in the signal such as various vibrational absorption bands. In other embodiments, user interface 1002 may simply display a test result such as "positive," "negative," or "inconclusive." It is contemplated that the electronic components and the order shown in FIG. 10 is only one possibility according to certain embodiments of the present disclosure. None of the electronic components shown in FIG. 10, whether alone or in combination with each other, should be construed as necessary, critical, or essential for the functionality of the present disclosure. It is further contemplated that other electronic components not shown may replace or be added to the components currently shown in FIG. 10.

In other embodiments not shown, similar biophotonic diagnostic methods are performed between a set of compression paddles. This embodiment may comprise a set of compression paddles with one or more light sources and one or more light detectors and may be used by compressing a patient's breast and transmitting light from the one or more sources to the one or more detectors.

It is understood that embodiments presented herein are meant to be exemplary. Embodiments of the present disclosure can comprise any combination or compatible features shown in the various figures, and these embodiments should not be limited to those expressly illustrated and discussed.

Although the present disclosure has been described in detail with reference to certain configurations thereof, other versions are possible. Further, none of the elements or features discussed herein should be construed as necessary, critical, or essential for any particular embodiment of the present disclosure. Therefore, the spirit and scope of the disclosure should not be limited to the versions described above. The foregoing is intended to cover all modifications and alternative constructions falling within the spirit and scope of the disclosure as expressed in the appended claims, wherein no portion of the disclosure is intended, expressly or implicitly, to be dedicated to the public domain if not set forth in the claims.

What is claimed is:

1. A method for in vivo detection of a failed breast implant, comprising:
   providing a device comprising:
      a light source; and
      a light detector;
   applying said device to a surface of a patient's breast;
   transmitting light from said source at a first location of said surface such that at least a portion of said light scatters through said breast in a first banana-shaped photon path, said first banana-shaped photon path comprising a transmitting end corresponding to said first location and a receiving end adjacent to said first location;
   receiving at least some of said scattered light transmitted at said first location from said detector on a second location of said surface, wherein said second location corresponds to said receiving end of said first banana-shaped photon path, wherein said first banana-shaped photon path has a first penetration depth corresponding to a first distance between said first location and said second location;
   obtaining a first set of vibrational absorption characteristics of said breast based on said first banana-shaped photon path;
   adjusting said device to move said source to a third location of said surface at a second distance from said second location, wherein said second distance is greater than said first distance;
   transmitting light from said source at said third location of said surface such that at least a portion of said light scatters through said breast in a second banana-shaped photon path;
   receiving at least some of said scattered light transmitted at said third location from said detector on said second location, wherein said second banana-shaped photon path has a second penetration depth corresponding to said second distance, wherein said second penetration depth is greater than said first penetration depth;
   obtaining a second set of vibrational absorption characteristics of said breast based on said second banana-shaped photon path;
   analyzing a chemical composition of said breast based on said first and second sets of vibrational absorption characteristics, said chemical composition comprising at least breast tissue and silicone;
   based on said analyzed chemical composition, determining that at least one of said first or second sets of vibrational absorption characteristics comprises an indicator of abnormal silicone within said breast.

2. The method of claim 1, wherein said light has a wavelength in the red or near infrared region of the electromagnetic spectrum.

3. The method of claim 1, wherein said medical device further comprises a plurality of adjustable arms, each of said plurality of adjustable arms comprising a light source.

4. The method of claim 3, further comprising adjusting each of said adjustable arms to correspond to the anatomy of said patient's breast.

5. The method of claim 4, wherein said patient's breast comprises a silicone breast implant.

6. The method of claim 5, further comprising adjusting said adjustable arms to avoid detection of said silicone breast implant.

7. The method of claim 6, wherein said indicator of abnormal silicone is a peak in the vibrational absorption band between 2800-3400 $cm^{-1}$.

8. The method of claim 3, further comprising providing a user interface in communication with said device.

9. The method of claim 8, further comprising displaying an image on said user interface based on said digital signal, wherein said indicator of leaked silicone is highlighted in a contrasted color in said image.

10. The method of claim 8, further comprising displaying a textual test result on said user interface.

11. The method of claim 3, further comprising moving at least one of said adjustable arms in a first direction.

12. The method of claim 11, further comprising moving at least one of said adjustable arms in a second direction.

13. The method of claim 12, further comprising moving at least one of said adjustable arms in a third direction.

14. The method of claim 1, wherein said device comprises:
   a base comprising a first adjustable arm, said first adjustable arm comprising a first light source internal to said first adjustable arm, wherein said first adjustable arm is configured to move in at least three directions relative to said base; and a housing attached to said base, said housing comprising electronic components.

15. The method of claim 14, wherein said first adjustable arm is configured to move radially, angularly, and laterally with respect to said base.

16. The method of claim 14, wherein said base further comprises:
- a second adjustable arm, said second adjustable arm comprising a second light source internal to said second adjustable arm;
- a third adjustable arm, said third adjustable arm comprising a third light source internal to said third adjustable arm; and
- a fourth adjustable arm, said fourth adjustable arm comprising a fourth light source internal to said fourth adjustable arm,
- wherein said detector is between said first, second, third, and fourth light sources.

17. The method of claim 16, wherein said surface has a nonplanar shape.

18. The method of claim 17, further comprising adjusting said first adjustable arm to correspond to said nonplanar shape of said surface.

19. The method of claim 16, further comprising operating said device with one hand.

20. The method of claim 19, further comprising adjusting said first adjustable arm automatically with one hand.

* * * * *